(12) United States Patent
Fabry et al.

(10) Patent No.: US 8,193,119 B2
(45) Date of Patent: Jun. 5, 2012

(54) ACID COMBINATION ONE STEP REACTION PROCESS FOR AGRICULTURAL USE PRODUCTS AND ASSOCIATED METHODS

(75) Inventors: Carl J. Fabry, Orlando, FL (US); Vaughn Astley, Lakeland, FL (US)

(73) Assignee: Plant Food Systems, Inc., Zellwood, FL (US)

( * ) Notice: Subject to any disclaimer, the term of this patent is extended or adjusted under 35 U.S.C. 154(b) by 0 days.

(21) Appl. No.: 13/035,779

(22) Filed: Feb. 25, 2011

(65) Prior Publication Data

US 2011/0183843 A1    Jul. 28, 2011

Related U.S. Application Data

(60) Continuation-in-part of application No. 13/019,564, filed on Feb. 2, 2011, which is a division of application No. 11/349,064, filed on Feb. 6, 2006, now Pat. No. 7,887,616.

(60) Provisional application No. 61/308,569, filed on Feb. 26, 2010, provisional application No. 60/650,378, filed on Feb. 4, 2005.

(51) Int. Cl.
  *C05D 1/00* (2006.01)
  *C01B 25/163* (2006.01)

(52) U.S. Cl. ............ 504/101; 71/34; 71/41; 71/48; 423/307

(58) Field of Classification Search ......... 71/32, 41, 71/48; 423/307; 424/601; 504/101
  See application file for complete search history.

(56) References Cited

U.S. PATENT DOCUMENTS

| | | | |
|---|---|---|---|
| 3,171,733 A | 3/1965 | Hignett et al. | |
| 3,464,808 A | 9/1969 | Kearns | |
| 3,788,817 A * | 1/1974 | Kolbe et al. | 422/198 |
| 3,950,495 A | 4/1976 | Ries | |
| 3,985,538 A | 10/1976 | Hicks et al. | |
| 4,601,891 A | 7/1986 | McGill et al. | |
| 4,637,921 A | 1/1987 | Sansing et al. | |
| 4,724,132 A | 2/1988 | Fabry | |
| 5,736,164 A | 4/1998 | Taylor | |
| 5,800,837 A | 9/1998 | Taylor | |
| 5,925,383 A | 7/1999 | Taylor | |
| 5,997,910 A | 12/1999 | Taylor | |
| 6,338,860 B1 | 1/2002 | Taylor | |
| 6,509,041 B2 | 1/2003 | Taylor | |
| 7,708,799 B2 * | 5/2010 | Grech et al. | 71/29 |
| 2002/0039970 A1 * | 4/2002 | Roberts et al. | 504/206 |
| 2003/0029211 A1 * | 2/2003 | Sheppardson et al. | 71/33 |

FOREIGN PATENT DOCUMENTS

WO    WO 2005110091 A1 *   11/2005

* cited by examiner

*Primary Examiner* — Wayne Langel
*Assistant Examiner* — Syed Iqbal
(74) *Attorney, Agent, or Firm* — Ralph D. Chabot

(57) ABSTRACT

A process for the manufacture of an aqueous composition that is a combination of a fungicide and fertilizer comprising the following steps:

(1) dissolving phosphorous acid in phosphoric acid to form a solution of an acid mixture;
(2) reacting the acid mixture of step (1) with an aqueous potassium hydroxide solution at a temperature of about 65° C. to about 260° C. in a continuous reactor while maintaining the ratio of potassium to phosphorous in various mole ratios thereby forming a reaction mixture comprising potassium phosphates, potassium polyphosphates, potassium phosphites, and potassium polyphosphites and potassium phosphate phosphite copolymers; and,
(3) cooling the reaction mixture rapidly at least 1° C. to 60° C., to below about 35° C. to about 65° C.

Using a similar process a composition having fungicidal properties is prepared by reaction phosphoric acid with potassium hydroxide.

The reaction mixtures prepared according to each of the above processes are also part of this invention.

22 Claims, 2 Drawing Sheets

NMR Spectra, Example 1

Sample #003, Showing P-H Bond Present After Reaction

ACID COMBINATION ONE STEP REACTION PROCESS FOR AGRICULTURAL USE PRODUCTS AND ASSOCIATED METHODS

CROSS-REFERENCE TO RELATED APPLICATION

This application claims the benefit of U.S. provisional application 61/308,569 filed Feb. 26, 2010, which is hereby incorporated by reference in its entirety for all purposes; and claims benefit to U.S. utility application 13/019,564 filed Feb. 2, 2011 which claims the benefit of U.S. utility application Ser. No. 11/349,064 filed Feb. 6, 2006 issued as U.S. Pat. No. 7,887,616.

FIELD OF THE INVENTION

This invention is directed to a process for the manufacture of potassium polyphosphate-potassium polyphosphite polymeric compounds, useful for agricultural purposes, as a fungicide or a fertilizer.

BACKGROUND OF THE INVENTION

Current commercial methods for making potassium salt compositions from phosphoric acid and phosphorous acid (Phosphorus (P) acids) are carried out by a process by separately manufacturing each potassium phosphorus salt. This is accomplished by charging each Phosphorus (P) acid with an aqueous base metal hydroxide solution, e.g., potassium hydroxide or potassium carbonate, or other base metal solutions, to a mixing tank equipped with an agitator and cooling means.

As a first step or stage and by an individual process for each acid, a base potassium solution is combined with a mineral acid. As an example a significant quantity of water is added to a typical 1,000 gallon open batch tank. Then 50 pound bags of dry mono potassium phosphate (MKP), which is not completely soluble, are slowly and partially dissolved by continuous agitation and kept agitated while dry bagged potassium hydroxide (KOH) is added. This is a slow, labor intensive, and not a very productive process which only generates a reaction temperature under about 40° C., because MKP is already mostly reacted to a near neutral pH and not very much KOH needs to be added in order to achieve a balanced analysis and pH.

Then as a second step or stage, by an individual process, a base potassium solution is combined, also separately, with a second mineral acid. As an example water is added to a typical 1,000 gallon agitated batch tank and then alternately 50 pound bags of phosphorous acid and KOH are is combined slowly in order to keep the reaction temperature as low as possible in order to prevent a "run away" reaction and the generation of phosphine gas. The process is very labor intensive, slow and unproductive and is capable of low analysis only.

Thirdly, an additional required step remains wherein these two individually produced potassium salts of each phosphoric and phosphorous acid must be pumped into an agitated batch tank and cold blended to produce a final useful, mixed solution. This is a complicated labor intensive, time consuming, inefficient process which requires additional equipment and storage tanks, and offers more opportunities for error in producing the final product.

In other processes, involves the use of phosphoric acid or by dissolving or wetting of potassium phosphates, such as mono or dipotassium phosphates, and are subject to a number of problems. The reason that the use of such mono and diphosphates is desirable in these time proven processes is that most of the exothermic reaction has been completed, thus lending these processes to a safer and simpler but more costly process.

Less common and more dangerous is reacting phosphoric acid and potassium hydroxide or carbonate directly in order to produce the desired mixtures of the desired P (phosphorus) and K (potassium) content.

The reaction can be violent and, on a large scale, even with good agitation and cooling, the reaction can "runaway" and result in fatalities and injuries. During the early stages of this process with either Phosphorus (P) acid, even if the reaction does not "runaway", localized excessive heat release occurs, at under 200° F. (94° C.), and in the case of the phosphorous acid, it is well known in the art that hazardous, toxic phosphine (hydrogen phosphide) gases physically characterized by garlic like odorous fumes which have decomposed, from the reaction, and are emitted from the batch type reactor which can create a hazard if not properly absorbed and disposed of. In addition, oxygen can very readily be absorbed into phosphorous acid, with the counterproductive decomposition result of the oxidation and formation of ortho-phosphoric acid.

In addition to being more labor intensive, other problems incur in these batch processes due to the necessarily slow addition of materials, in order to prevent "runaway" reactions and the decomposition of phosphorous acid. More problematic is that there is insufficient heat generated with either acid, in the initial part of the reaction with the metal hydroxide solution, thus, preventing the formation of the polymers of phosphorous acid, or of phosphoric acid by heat of reaction. As a consequence, previous processes provide no polymeric conversion of ortho-phosphorous acid to poly-phosphite and ortho phosphite compounds, or ortho phosphoric acid to polyphosphate and ortho phosphate compounds, because of the imbalance of reactants and/or the temperature required for the conversion.

Another potential problem which occurs in a batch process is satisfactorily achieving the final pH because extreme caution must be observed in the final stages of the reaction because of the real potential of overshooting the final pH by over addition of either the acid or the base. Precautions must be taken in measuring the ingredients precisely. Careful monitoring is time consuming and lack of attention could lead to an explosion due to a "runaway" chemical reaction. Further, the batch process is known to be more labor intensive and with higher production costs.

U.S. Pat. Nos. 5,736,164; 5,800,837; 5,997,910; 5,925,383; 6,338,860 and 6,509,041 in general describe the blending of individually prepared solutions of ortho potassium phosphate and ortho potassium phosphite, utilizing only mostly reacted MKP and KOH, by a "batch" process as described above. The processes disclosed are generally labor intensive because dry bagged reactants are carefully, individually added to the batch processes where it is important to keep any heat of reaction as low as possible; because, as in the case of blending phosphorous acid with a base reactant, extreme caution must be exercised in order to prevent "runaway" reactions and to keep the temperature low enough so that poisonous phosphine gasses are not emitted. In any case, phosphate or phosphite polymers are not formed because the high temperatures necessary to produce polymeric compounds are not achieved in a batch process.

Then secondly, in the case of formulating a potassium phosphate solution according to the methods herein described, by a second step mono potassium phosphate is dissolved by the addition of water and further neutralized to desired levels generally with potassium hydroxide.

Both potassium phosphate and phosphite solutions herein described from 1996 have long been recognized by the Association of American Plant Food Control Officials (AAPFCO) as fertilizer ingredients as being useful for agriculture and their subsequent use in combined fertilizer mixtures. These patents do not disclose bactericidal attributes.

Then finally, the two individually prepared solutions are "cold blended" combining the two solutions in a third step.

Further, each of the processes disclosed by these patents have one or more of the above problems and disadvantages.

A critical component for all plant growth is the phosphate ion, $PO_4^{3-}$. The phosphate ion can readily be applied to crops from easy to use aqueous solutions of ortho or ammonium polyphosphate or ortho potassium phosphate, which are important components of modern agriculture, primarily for soil application. However, these solutions are physically and agronomically unstable when foliarly applied to crops with little or no agronomic benefit, and can cause significant crop injury. Typically, these ammonium and potassium phosphate solutions are prepared by an acid base reaction, i.e., ammonia and ammonium hydroxide and potassium hydroxide are reacted with phosphoric acid.

Commercial processes are shown for the preparation of ammonium polyphosphate in Hignett et al. U.S. Pat. No. 3,171,733 and Ries U.S. Pat. No. 3,950,495. Hicks et al. U.S. Pat. No. 3,985,538 shows the use of a pipe reactor to prepare ammonium polyphosphate. These processes result in the conversion of some of the normal ortho phosphates to polyphosphates. Processes for improving yields are shown in Sansing et al. U.S. Pat. No. 4,637,921, McGill et al. U.S. Pat. No. 4,601,891, Kearns U.S. Pat. No. 3,464,808 and Ries U.S. Pat. No. 3,950,495. Fabry U.S. Pat. No. 4,724,132 shows a continuous process for the manufacture of a metal salt solution useful for fertilization.

There is a need for a novel process, as provided by this invention that does not rely on the use of MKP in order to form compositions that provide useful agricultural products that not only provide potassium ortho phosphates and ortho potassium phosphites in a single solution but also in a novel way, compositions that also include potassium polyphosphates and potassium polyphosphites, in a more efficient, safer and more cost effective way, in order to provide a single combination product that is both a superior, more effective fungicide and a safe and effective fertilizer, useful for agriculture.

SUMMARY OF THE INVENTION

The present invention is directed toward a continuous process for the manufacture of an aqueous solution containing potassium polyphosphates and potassium polyphosphates compositions that can be categorized either as a fertilizer compound recognized by AAPFCO containing a phosphate and a phosphite, or as a pesticide compound recognized by the United States Environmental Protection Agency (EPA) as a fungicidal compound containing a phosphate and a phosphite, or any other possible combination of the two, potassium phosphates and potassium phosphites thereof as either fertilizers or pesticides; or, individual aqueous solutions of either poly phosphates or poly phosphates; the process comprises the following:

(1) dissolving dry phosphorous acid directly into liquid phosphoric acid, which minimizes or eliminates wasteful "free water", which would hinder the polymerizing reaction, to form a concentrated solution of an acid mixture resulting in a Dual Phosphorus (P) Acid Combination (DPAC) product; or, by blending a concentrated solution of phosphorous acid into liquid phosphoric acid to form a more concentrated solution of both acids, thus, resulting in greater reactivity in order to form Phosphorus (P) acid polymers; and (2) reacting the acid mixture of step (1) with an aqueous potassium hydroxide solution at a temperature of about 65° C. to about 260° C. in a continuous reactor while maintaining the ratio of potassium to phosphorus in various mole ratios thereby forming a reaction mixture comprising potassium phosphates, potassium polyphosphates, potassium phosphites, and potassium polyphosphites and potassium phosphate phosphite co-polymers and (3) cooling the reaction mixture rapidly from at least 1° C. to 60° C., to below about 35° C. to about 65° C.

The DPAC reaction mixture prepared according to the above process is also part of this invention which results in a pesticide composition or a fertilizer composition or any pesticide/fertilizer combination thereof.

Another aspect of this invention is a continuous process for the manufacture of a potassium ortho and polyphosphite solution which is a not only fungicidal and/or nutritional composition but bactericidal as well, in any combination, that has both pesticidal and/or fertilizer properties; also, continuously manufactured wherein phosphorous acid is dissolved in water in order to formulate a solution of phosphorous acid containing between 50%-80% phosphorous acid, which is then reacted with an aqueous potassium hydroxide solution to form aqueous potassium polyphosphites.

Another aspect of this invention is an acid mixture formed by dissolving dry phosphorous acid in phosphoric acid; or, by blending a solution of phosphorous acid with phosphoric acid thereby forming a useful intermediate product particularly useful for the formation of fertilizers and pesticides.

Both the DPAC reaction mixture and the potassium polyphosphite solution have both pesticidal and/or fertilizer utility and a method for applying an effective amount of either of the compositions is also part of this invention.

Other objects and advantages of the invention will become apparent to those skilled in the art upon reference to the detailed description that hereinafter follows.

DETAILED DESCRIPTION OF THE INVENTION

Figure 1:
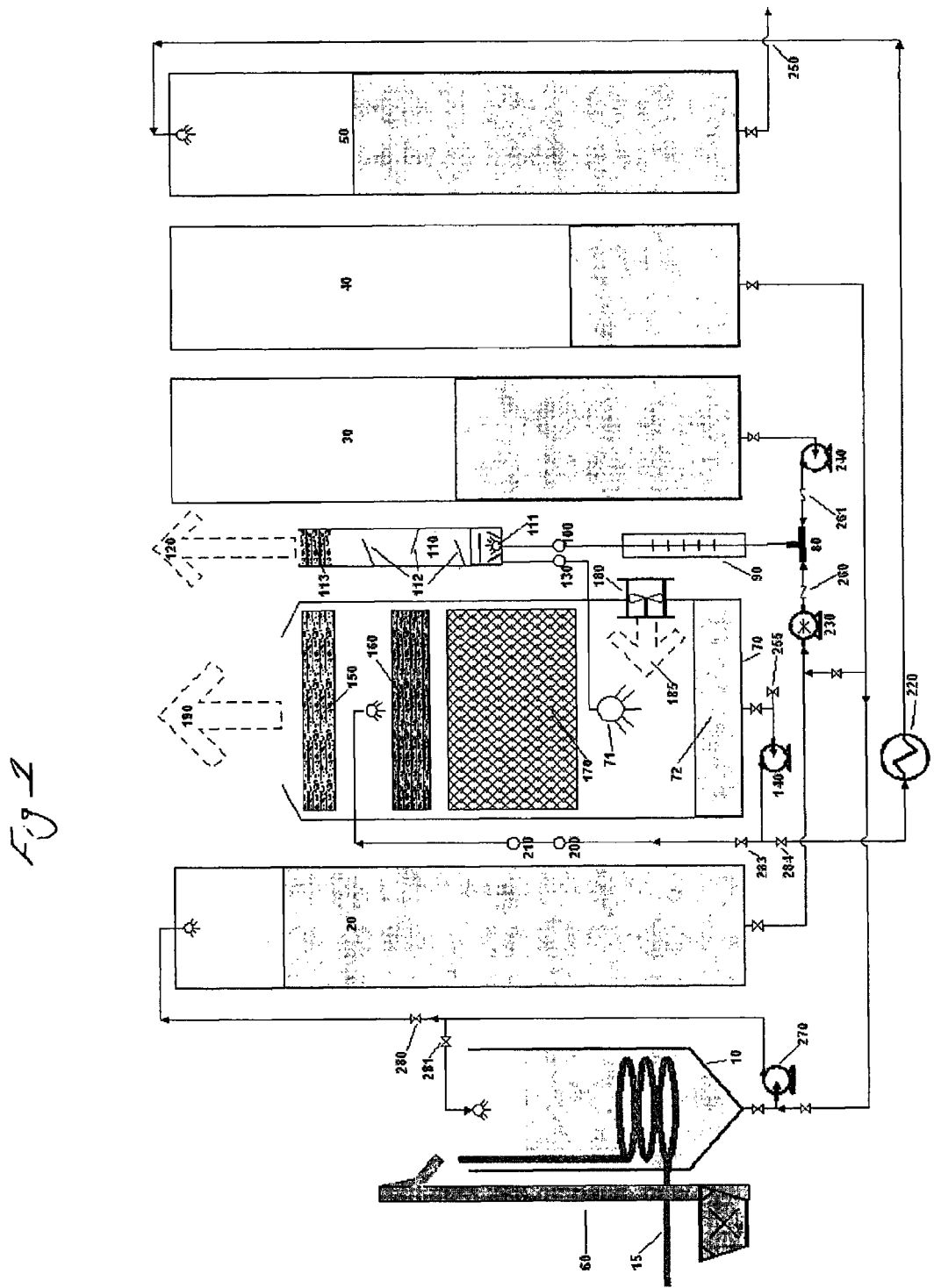
FIG. 1 shows a flow diagram of the process for making the fungicide and fertilizer composition of this invention.
Figure 2:
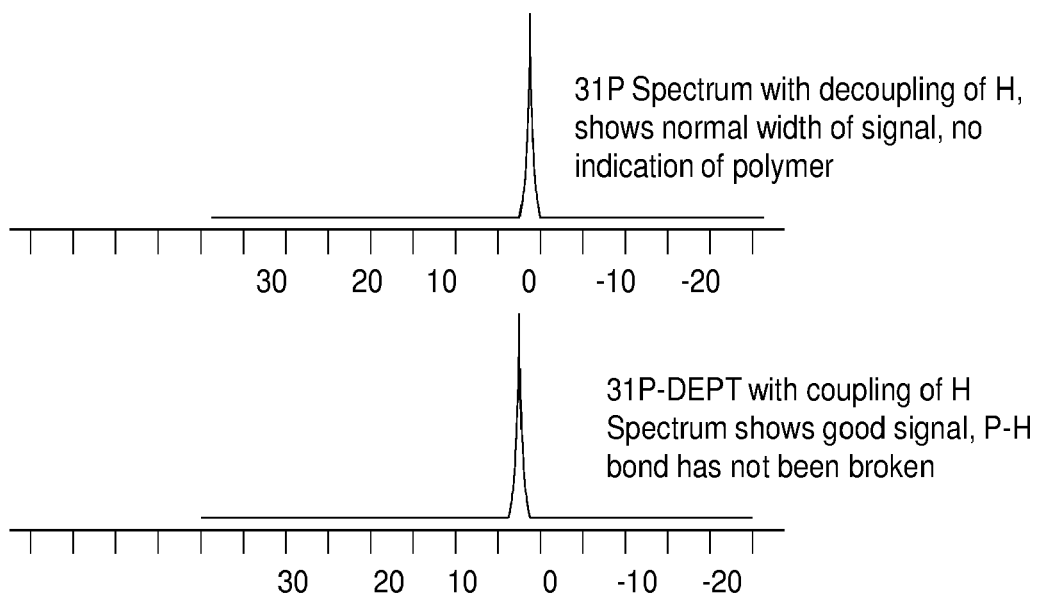
FIG. 2 shows an NMR spectra of the product of Example 1 showing the presence of P—H bond.

Applicant specifically incorporates the entire contents of all cited references in this disclosure. Further, when an amount, concentration, or other values or parameters are given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

In the context of this disclosure, a number of terms are utilized.

The term "about" means within 20%, preferably within 10%, and more preferably within 5% of a given value or range.

The term "comprising" is intended to include embodiments encompassed by the terms "consisting essentially of" and "consisting of". Similarly, the term "consisting essentially of" is intended to include embodiments encompassed by the term "consisting of".

The term "potassium polyphosphate(s)" means polymeric potassium phosphate polymers and includes oligomers, for example, dimers, trimers and the like.

The term "potassium polyphosphite(s)" means polymeric potassium phosphite polymers and includes oligomers, for example, dimers, trimers and the like.

The term "potassium phosphate-phosphite copolymer(s)" means copolymers of potassium phosphates and potassium phosphites.

The term "DPAC" (Dual Phosphorus Acid Combination) means a mixture of phosphorous acid dissolved in phosphoric acid; or, a solution of phosphorous acid blended with phosphoric acid.

The term "DPAC reaction mixture" means an aqueous mixture formed by the process of this invention comprising potassium phosphates, potassium polyphosphates, potassium phosphites, and potassium polyphosphites and potassium phosphate/phosphite copolymers.

The term "aqueous potassium polyphosphite solution" means an aqueous mixture formed by the process of this invention wherein aqueous phosphorous acid is reacted with potassium hydroxide and comprises ortho and potassium polyphosphites, mono-potassium phosphite, and or dipotassium phosphite and forms a pesticidal and/or nutrient solution.

In the preparation of the novel DPAC reaction mixture, a continuous reaction, single step process is used wherein DPAC is formed by combining phosphorous acid with phosphoric acid and then this DPAC mixture is reacted with potassium hydroxide under high heat of reaction followed by rapid cooling to form the DPAC reaction mixture.

The novel process of this invention provides a number of advantages over methods taught in the art. In a single step process, a fungicidal and fertilizer composition is prepared having polymeric components that have a higher analysis with long term storage stability allowing the composition to remain, as a clear solution, in storage for extended periods of time without "salting out", and remaining in a clear solution longer than conventionally produced orthophosphorus products. The polymerized products of this invention, and can be readily blended with other components, particularly sequestering inorganic metal compounds such as Copper, Iron, Manganese and Zinc to form higher analysis, stable compositions that reduce and many cases eliminate fungicidal activity on a wide variety of plants and crops and provides fertilizer components to plants and crops in particular, a polyphosphate which is well known to be beneficial to plants. Further, there is significantly less foliage burn caused when the products of this invention are applied directly to plants, because of the polymers present in the solutions of the invention. The polyphosphate and polyphosphate compounds of this invention are also capable of forming soluble complexes with metal impurities by a sequestration process; also, the compositions have activity as a pesticide.

An important aspect of the novel process, which has not been previously recognized, is that the DPAC can be formed by dissolving orthophosphorous acid directly in orthophosphoric or super polyphosphoric acid without additional of water thereby providing a high concentration of highly reactive acid when used in the process is capable of producing polymeric compounds. Less water is present in the novel process thereby concentrating the acid favorably for the formation of polyphosphorus compounds. Thus, polymer formation is facilitated and increased and the exothermic reaction temperature is higher causing an additional release of water to provide a high concentration reaction mixture and conversion containing phosphate and phosphite polymers, along with residual ortho phosphate and orthophosphate compounds. Further, degradation by hydrolysis of the potassium polyphosphites and related polymers is significantly reduced. With the use of a continuous reactor in the process, the risk of a "runaway" reaction is eliminated. The unwanted formation of any phosphine gas that often occurs in a batch reaction, which is very difficult to control, is eliminated by the complete, instantaneous reaction, and instantaneous cooling process below critical phosphine formation temperature levels. Only evaporative steam from the heat of reaction, from the novel process, is harmlessly discharged to the environment.

Following in general the flow diagram of FIG. 1, the novel process of this invention is illustrated for forming the DPAC reaction mixture. First a measured amount of phosphoric acid is pumped from tank 40 via centrifugal pump 270 though valve 281 either by weight, metering or by visual reference into blend tank 10. Then following, a dry phosphorous acid product from storage is transported, lifted and a measured amount is placed via an elevator 60 likewise into blend tank 10 for dissolving. Other means, either mechanical or labor intensive can be used to put the dry phosphorous acid into blend tank 10. As an option, a pre-dissolved aqueous solution of phosphorous acid can also be used in the place of dry phosphorous acid. Pump 270 is used to re-circulate the phosphoric acid in blend tank 10 through valve 281 in order to agitate the phosphoric/phosphorous acid combination in order to facilitate the dissolving process while the dry phosphorous is being added to the phosphoric acid. Additionally, any acceptable form of agitation can be utilized, including paddle agitation. Upon completion of the dissolving process, the resulting acid mixture, hereinafter "DPAC", can be pumped via the pump 270 through valve 280 into storage tank 20 or the DPAC can be recycled or agitated by pump 270 into blend tank 10 by changing the flow positions of valves 281 and 280.

The phosphoric acid used can be in any commercial or practical concentration, usually from 75% to a 115% $H_3PO_4$ concentration. A concentration over 96% is considered to be super phosphoric acid; however, the preferred concentration is from 85% to 105% for practical commercial acid purchase availability, handling and storage advantage. The DPAC can be in the range of 1-99 parts phosphoric acid to 99-1 parts phosphorous acid, preferably, about 90-50 parts phosphoric acid to 10-50 parts phosphorous acid.

KOH (potassium hydroxide) solution is stored in tank 30 and is pumped via a constant speed and flow rate pump 240 into the reactor tee 80 through a backflow prevention check valve 261.

The DPAC is pumped from storage tank 20 via a variable speed pump 230 through a backflow prevention check valve 260 into the reactor tee 80. The reaction of the impinging acid and base in the reactor tee is virtually instantaneous, and the reaction is further facilitated and evenly completed as the reactants flow through the inline static mixer 90, resulting in an instantaneous exothermic reaction that raises the temperature of the mixture to about 50° to about 260° C., preferably about 100° to about 200° C. By this continuous process, the reaction time and travel through the static mixer can be very swift depending on the production rate, usually measured in several seconds.

The ratio of the DPAC to KOH is maintained at various mole ratios, preferably up to about 2:1 and more preferably 1:1 to 2:1, by controlling and adjusting the flow rate of the Acid pump 230. The proper ratio of acid to base is thereby maintained and governed by proper adjustment of the variable speed pump 230, based on the constant monitoring of both the pH and the specific gravity of the reactants as the appropriate adjustments are then made to pump 230 as the DPAC is injected into the reactor unit 70, while pump 240 stably pumps the KOH solution at a constant rate into the reactor 70. As a result the reaction mixture is passed efficiently and accurately through the static in-line mixer 90 where the reaction of KOH and DPAC is completed to the desired specifications.

The KOH solution is an aqueous solution, manufactured and can be purchased and received as such (or formed from dry flake KOH) that contains about 25-95 wt %, preferably about 40-60 wt % and more preferably about 50 wt % KOH.

The reactor tee 80 is a typical conventional reactor custom manufactured and assembled on site in a "tee" configuration to the proper specifications. Any conventional continuous reactor known to those skilled in the art can be used but reactor tees connected with a tubular pipe section to the static inline mixer are preferred. Useful reactor tees and their tubular components can vary in diameter from about 1-12 inches or more in diameter, depending on the desired production flow rate, residence time desired for the reaction for optimum polymer formation, and by other factors. The diameter and length of the continuous reactor, typically tubular, are critical factors; however, the ratio of length to diameter is most useful. The ratio of length to diameter should be between about 20 and 5. A more preferred ratio is between 15 and 6.

Typically, a 2 inch diameter tubular reactor is used wherein the KOH solution is pumped into the reactor at a rate of between about 20 and 40 gpm with the preferred rate being about 29 gpm. DPAC is pumped into the reactor at a rate between about 15 and 40 gpm with the preferred rate being about 21 gpm. Temperature control is achieved primarily by simultaneous and proportional flow reduction or increase of the DPAC. The "high" reaction temperature is measured in the reactor in the pipe leading from it via a thermal gauge 100. The process temperature is between about 65° C. and about 260° C. Either or both of the reactants may be preheated by various means, an outside heat source or including heat transfer from the reaction or the finished product cooling, in order to reach temperatures higher than about 175° C., while maintaining sufficient cooling.

The actual residence time in the reactor tee 80, through the static mixer 90, the piping and prior to entering steam disengagement unit 110, is very rapid because of high flow rates and the instantaneous removal of water by the heat of reaction, resulting in the generation of steam. The residence time is calculated from the volume of the reactor tee 80, through the static mixer 90, the piping and prior to entering steam disengagement unit 110, divided by the volume pumped in per minute. The residence time calculated in this manner is preferred to be between about 0.01 and 1.5 minutes. A more preferred residence time is between about 0.02 and 1.0 minute; however longer residence times could produce even higher polymer content.

The reactor tee 80 is used in combination with static in-line mixer 90 which facilitates complete reaction; although, a sufficient reaction is possible without such a peripheral inline mixing device in conjunction with the reactor tee. A typical in-line mixer useful in the process of this invention is disclosed in Horner U.S. Pat. No. 4,093,188. This particular in-line mixer has stationary baffles providing sinuous, non-parallel spiraling path to effect a more thorough and efficient blending of fluids. Other conventional static in-line mixers can be used in the process as disclosed in Katzen U.S. Pat. No. 3,190,618, Chisholm U.S. Pat. No. 3,652,061 and Sluijters Re. 28,072. The length and configuration of the in-line mixer is such that the reaction is substantially completed before cooling of the reaction mixture. If an in-line mixer were not used in the process, the tubular reactor would have to be lengthened to insure a substantially complete reaction.

Thermal gauge 100 measures the temperature of the reaction mixture as it leaves the static in-line mixer 90. It is essential that the temperature of the reaction mixture be maintained in about the 50° to about 200° C. range in order to produce the highest polymer content possible while preventing hydrolyzation of polymers formed in the reaction mixture by residual water that may be present. However, it is essential to maintain the reactor vessel temperature below about 70° C. and product temperature to storage below about 35° C. in order to minimize hydrolysis of polyphosphates back to the ortho form. The reaction mixture is then passed into the steam disengagement unit 110 wherein the temperature of the reaction mixture is rapidly reduced at least about 25° C. below the reaction temperature and to below about 25° to about 75° C. Typically, if the reaction temperature is about 200° C., the temperature should be rapidly reduced to about 65° C. and then further reduced to about the 30° to about the 40° C. range. Variations in the rapid reduction of the temperature will be required depending on the initial temperature of the reactants, the concentration of the reactants and the like. In this unit, water in the form of steam 120 is instantaneously released from the reaction mixture and vented to the atmosphere and accounts in part for the necessary first step in the rapid temperature drop of the reaction mixture in order to preserve polymer content. Rapid cooling is important in order to obtain and preserve high yield of polyphosphates and polyphosphites in order to reduce the hydrolysis reaction or other degradation of the polymers formed.

The steam disengagement unit 110 comprises a pressure reduction nozzle 111 which reduces the temperature of the reaction mixture by diffusing the reactant pressure, evacuating steam by a series of baffles 112 which further provide a reduction of temperature and a demister pad 113 that prevents loss of reaction mixture which condenses on the pad and flows back into the unit 110. Steam 120 condenses to water vapor as it passes out of the unit to the atmosphere. The reaction mixture then passes through to the evaporative cooling tank 70, through temperature gauge 130, and out through a spray nozzle 71 which further disengages any residual steam and the reactant is then further cooled by air by an axial flow evaporative cooling fan 180 to further reduce the temperature of the reaction mixture to desirable levels. Evaporative cooling is typical to those familiar with the art. Ambient temperature air 185 is injected, blown, and forced through packing element 170 while the hot reactant product is recirculated by pump 140 through valve 283 through temperature gauge 210 and pH meter 200 exiting onto a fluid diffuser plate 160 and passing through the packing 170 in which the packing comprises shaped pieces of polyvinyl chloride and reactant flowing down through that packing, evaporatively cooling, and on down to the bottom of the reaction tank 70. As air passes up through the packing 170 while simultaneously the hot reactant is passing down over the packing 170, steam and heat 190 is released which passes through the diffuser plate 160 and up and out through the demister pad 150 which serves to prevent any blown reactant passing on through harmlessly to the atmosphere and to the environment.

Pump 140 not only pumps hot reactant over the packing for cooling, but also simultaneously bypasses and directs a certain portion of that production flow of now cooled and finished reactant, now product, through a metering finished product storage control valve 284 to the final product storage tank 50. Production balance, between the reactants going into the process, evaporation losses together with maintaining a constant fluid level in the process control tank and cooling tower result in a continuous equilibrium between production and storage. The, reactor level control is maintained and cooling as measured by temperature gauge 200 and a pH of about 6.00 to about 8.50 measured by pH meter 200 is achieved by carefully monitoring and controlling the production flow rate through the reactor tee by maintaining a steady reactant product heel level 72 in the cooling tower tank 70. If additional cooling is required in order to maintain and preserve maximum polymer content, a conventional heat exchanger 220 such as, a plate and frame or tube and shell, can be added prior to delivery in to the product storage tank 50. The resulting product is then sent to product storage tank 50 through product control valve 284, for ultimate shipping and distribution via product storage tank valve 250.

In reference FIG. 1, the size of the tanks 10 and 20 containing acid or the potassium hydroxide tank 30 is immaterial as long as they contain sufficient material to produce a continuous reaction and the desired amount of product. A separate tank that contains other minor ingredients, such as secondary nutrients and micronutrients, can be used in the process but these minor ingredients are not utilized to such an extent to significantly change the ratio of the DPAC to KOH solution in the reaction. The tubular reactor (reactor tee 80) only functions using liquid feeds resulting in liquid product. Hence, the DPAC and the KOH solution must be liquids.

Similarly, an aqueous potassium polyphosphite solution is prepared using the above process as shown in FIG. 1 with slight modifications to the process. Phosphorous acid is dissolved in water in acid storage tank 10 wherein the phosphorous acid fluid concentration is about 50%-80% phosphorous acid, and 80% ideally. The aqueous phosphorous acid solution is pumped into storage tank 20 and then to the reactor tee 80 as described above with KOH solution from storage tank 30. The aqueous phosphorous acid solution is fed into the reactor tee 80 at a rate of about 10 to 20 gallons per minute simultaneously with the aqueous potassium hydroxide solution which is being fed into the reactor at a rate of about 20-30 gallons per minute and the acid and potassium hydroxide are reacted for about 0.01-1.5 minutes. The ratio of potassium to phosphorus in maintained in a molar ratio of about 2:1 to about 3:1. The reaction is an exothermic reaction that raises the temperature of the mixture to about 65° C. to about 260° C. The resulting reaction mixture is passed into static in-line mixer 90 where the reaction with KOH is completed. The time the mixture is in the reactor tee 80 and the static mixer 90 is about 0.01-1.5 minutes. The resulting reaction mixture, hereinafter, aqueous potassium polyphosphite solution, is passed into the steam disengagement unit 110, described above and into reaction vessel 70, described above, and rapid cooling is achieved as described above. Essentially, the temperatures and reaction times in the process are the same or very similar to those described above. As noted above, rapid cooling is important to obtain high yields of polyphosphite and reduce any hydrolysis reactions or other reactions that would degrade polymer formed. The aqueous potassium polyphosphite solution is then pumped through heat exchanger 220 and to tank 50 and then sent to product packaging or distribution.

During both the DPAC reaction mixture process and the Polyphosphite" process, specific gravity and pH is measured continually during the process in motion from a small, recirculated continuous side stream of product going to storage through product tank valve 200. By this constant measurement of constant production, end product quality is continually assured throughout the entire process.

The reactor process efficiently utilizes heat of reaction to produce the energy required to polymerize orthophosphates and orthophosphates to poly phosphates and polyphosphates. The entire reaction is contained to the limited volume of the upper portion of the reactor tee 80, from which the temperature continues to increase up through the inline static mixer 90. By dissolving phosphorous acid directly in phosphoric acid, most of the free water is eliminated and the dehydrolyzation reaction to polymerization facilitated.

Potassium phosphate solutions, MKP solutions and dipotassium phosphate solutions manufactured by the batch process only capable of producing orthophosphate and orthophosphite. Batch produced product is of low and questionable analysis, readily precipitates or salts out with limited storage shelf life, is not capable of being blended with inorganic micronutrient compounds without precipitation, and has limited agronomic benefit and questionable pesticidal benefit. While limited fungicidal benefits can be achieved, no orthophosphate of orthophosphite or any combination thereof product produced by the batch method is known to also have bactericidal control properties. While the present invention also produces of orthophosphate and orthophosphite, the added production of a high percentage of polyphosphates and polyphosphites, within a single solution is unique and significantly contributes to extended shelf life as a clear solution without precipitation or salting out. Probably the single most unique property of the invention is that not only does it exhibit superior plant nutritional qualities, but excels as a fungicide, but more importantly has been shown to be a superior bactericide as well.

It should be noted that a batch process particularly one utilizing MKP, uses a significant amount of water. The result is a less concentrated solution not capable of polymer formation, is more labor intensive, less safe and less efficient; but never the less, can be used to produce useful reactant Phosphorus products. Typically batch processes use a stirred tank reactor, to slowly, with great care in order to avoid a dangerous "run-away" reaction, react potassium hydroxide and phosphorous acid or the DPAC. However, the temperature and process conditions must be controlled very accurately with adequate safeguards out in a batch reaction. In particular, temperature control of the reaction is very difficult and if not controlled, a "run-away" reaction can occur and toxic phosphine gas can be formed at temperatures above about 65° C. Further, a batch reactor is significantly slower in reaction and is difficult to seal and prevent atmospheric oxygen from entering which readily oxidizes phosphorous acid to ortho phosphoric acid, thereby preventing the formation of phosphites. In the closed continuous process as set forth above, phosphine gas is not formed since a continuous reactor (tubular reactor) is used wherein temperature and reaction conditions are controlled to prevent the formation of such toxic products.

An unexpected and important advantage of the process for forming a DPAC reaction mixture is that polyphosphate and polyphosphite can be prepared simultaneously. The process of this invention produces high yields of polyphosphate if a mixture of phosphorous acid and phosphoric acid is used instead of phosphorous acid alone. The advantages of having a mixture of both acids include less handling, lower manufacturing, storage, and blending costs; however, the most important advantage of the DPAC reaction process is that bactericides are also produced. The DPAC reaction mixture now allows simultaneous application of a fungicide, a bactericide, and a fertilizer, the co-application of which enhances crop growth in a synergistic effect, more so than if each material was separately applied. The presence of nutrients makes possible quick, vigorous growth of the crop enabling the crop to more effectively compete with pests held in check the DPAC's fungicide and bactericide combination, thereby increasing the effective utilization of the fertilizer. Applying nutrients in combination with a fungicide and a bactericide will enhance the effectiveness of the fungicide and bactericide on its pest on target. Also, the presence of both acids in the process provides for the formation of copolymers, that is, polymers containing both phosphite and phosphate groups. Such copolymers are new materials and not simply a mixture of polyphosphite and polyphosphate. However, chemical analysis of such polymers is difficult.

The novelty of this DPAC reaction mixture is that it provides simultaneous fungicidal activity to plants and fertilizer to plants. In particular, potassium phosphite provides fungicidal activity and the potassium polyphosphite is a superior fungicide and when these two components hydrolyze after application and exposure to the elements, they form phosphate ions that fertilize the plant.

Recent studies have shown that plants when treated with phosphites will absorb and store phosphites. However, plants cannot use phosphites as a phosphorus nutrient source, but require that phosphates be applied in order to meet plant phosphorus needs. The absorption and storage of phosphite triggers a mechanism in the plant wherein the plant will not absorb phosphate which is the nutrient the plant requires and the plant will exhibit the characteristics of phosphate starvation. Therefore, the phosphate compounds in the DPAC reaction mixture are an absolute necessity to provide ortho-phosphorus to the plants that is absorbed by the plants and provides the fertilizer component that is required for plant growth and development.

The DPAC reaction mixture can be blended with components, such as, urea or other ammonical compounds to provide a nitrogen component and also with effective amounts of secondary nutrients such as, calcium, magnesium, sulfur, and micronutrients such as, boron, copper, iron, molybdenum, manganese and zinc to form a high quality fungicide, bactericide and a fertilizer. Also, the reaction mixture can be cold blended with a variety of agriculture products for application by growers or can be sold as an intermediate to growers to blend with other agricultural products. Stable clear and sprayable compositions are formed.

Typically, the DPAC reaction mixture after manufacture and as kept in storage has an N/P/K of, 0-23-25 to a 0-26-26, and then is cold blended with water for sale to a customer and has an N/P/K in the range of 0-28-25 to 0-30-27. The DPAC reaction mixture is sprayed onto crops in an effective amount depending on the crop and the desired effect that is wanted to reduce damage and or fertilize the crop.

The DPAC used in the novel process is unique since it has not been previously disclosed that phosphorous acid can be dissolved in phosphoric acid without the use of a significant amount of water. High acid concentrations can be achieved particularly since super phosphoric acid can be used. The DPAC is useful as an intermediate not only in the novel process but also in the formation of other fungicidal and fertilizer products.

The aqueous potassium polyphosphite solution prepared according to this invention is a fungicidal and bactericidal composition; never the less, fertilizer compositions utilizing the same ingredients are also recognized by AAPFCO . . . . Potassium phosphite provides fungicidal activity but the potassium polyphosphite is a superior fungicide and when the phosphite becomes hydrolyzed after application phosphate ions are formed which provide fertilizer to the plant. All the products of this invention are recognized and can be cold blended with most other fertilizer nutrient materials, particularly most inorganic metal compounds.

The prior art processes directed to forming polyphosphates do not teach the formation of polyphosphites. Polyphosphites have not been reported in the literature except for the combination of two units and it is only listed as a substance in the CAS Registry under "Pyrophosphite, #1710136-9. The absence of any disclosures on the preparation of polyphosphite versus polyphosphates is understandable in view of the higher reactivity, instability of phosphorous acid and phosphite and the potential for the formation of dangerous gasses. For instance, phosphite is readily converted to phosphate in soils and phosphorous acid is a much stronger acid than phosphoric acid. Therefore, polyphosphites are expected to be more sensitive to hydrolysis than polyphosphate. Furthermore, analysis of phosphite compounds is complicated by standard practices in the agriculture industry and by the reactive nature of phosphites; and, current analytical procedures are limited to phosphorus determination only. The agriculture industry relies on analytical methods for phosphorous as prescribed by, The Fertilizer Institute (TFI) or the American Organization of Analytical Chemists, (AOAC). Neither of these organizations recognizes the more recent role that phosphites play in agriculture today because they have been evaluated for their nutritional value only, by soil application. Because a new and novel salt of phosphorous acid has been created by this invention, there is no direct readily available wet chemical method for phosphites, and Phosphorus determination must be specially made by AOAC method 960.02, which is different from normal phosphorus determination methods. The standard methods for phosphorous published by the TFI or AOAC convert the reactive phosphite to phosphate and the results are published as phosphate, not phosphite. It is possible to deduce the amount of phosphite by quantitative measurement of chemical reducing power in the sample but this technique is fraught with much difficulty. Physical methods can be used such as by $^{31}P$ quantitative nuclear magnetic resonance (NMR), which in most cases can distinguish between the two types of phosphorous atoms, $PO_4^{3-}$ and $HPO_3^{2-}$. Typically, analytical laboratories determine total $P_2O_5$ for, or as, ortho phosphate using the approved industry standard methods which utilize the phospho-molybdate colorimetic analytical procedure. All other phosphate species which do not analyze as "ortho phosphate", are non ortho species, and are relegated as "polyphosphites and reported as such. This procedure is easier to understand for "ammonium polyphosphate" determinations, because there is no other possible source of "non ortho" species except polymerized species; however, in the case of simple phosphorous acid compounds, all the phosphorus therein also analyzes as a "non ortho" species and is therefore also assigned its value totally, for the entire sample as a "polyphosphate, confusingly as well.

In the present invention this problem is solved by knowing the amount, or the ratio, of ortho phosphorous acid present, and/or to the ortho phosphoric acid present in the solution. When the total phosphate, and the ortho phosphate (because of the presence of ortho phosphoric acid) value is reported, and the balance assigned as total polyphosphate content, the known value or contribution of the phosphorous acid present, to the total polyphosphate value, can then be subtracted and the balance then reliably to be true, formed polyphosphate, as illustrated in table 1-1 below.

However the most effective and practical way to determine if polymers of phosphoric or phosphorous acid have been produced, is by comparing the physical difference and the physical properties of ortho solutions as compared to those differences and properties of this invention. The following are all physical characteristics and attributes of ammoniated polyphosphates which compare favorably with those potassium salt based polyphosphates and poly phosphites of this invention, as compared to orthophosphates and orthophosphites, which include: significantly higher analysis, longevity in storage without precipitation or "salting out", remaining a crystal clear solution, blending capability with inorganic metal nutrient compounds with little or no precipitation, and significantly better crop response.

The following examples illustrate the invention. All parts and percentages are on a weight basis unless otherwise indicated.

EXAMPLES

Example 1

Referring to FIG. 1, first a measured amount of 85% phosphoric acid was pumped from tank 40 via pump 270 into blend tank 10. Next, solid dry 99% phosphorous acid was transported to blend tank 10 and lifted into blend tank 10 via elevator 60 and blended, agitated and mixed with pump 270 with the 85% phosphoric acid and dissolved therein. A continuous feed ratio of 1:3 by weight of phosphorous acid to phosphoric acid was maintained during the process. The resulting DPAC was then preheated by an external source of steam through heating coil 15, from ambient temperature to about 82° C. in order to obtain a higher heat of reaction temperature in reactor tee 80. To begin the test, a 3,000 gallon per hour production rate was established which would require a 29 GPM per minute flow rate of KOH and 21 GPM flow rate of phosphoric acid when production was fully up to specification. A "resident" 300 gallon starter heel of finished product was left in the reactor vessel from the previous run in order to prime the evaporative cooling system with similar product so that cooling of the first, hot reacted product entering the reactor vessel would be instantaneous. The process can also be started up using a water heel for instantaneous evaporative cooling, but is not as desirable as starting up on finished goods because this water dilution of the initially produced product needs to then be worked off during the entire run and can result in a lower polymer concentration. The variable speed KOH pump 240 was started at the full anticipated flow rate of 29 GPM. A constant speed pump can also be used with a manifold by pass system with two distribution valves on the discharge side of the pump. One valve can direct the appropriate amount of product on through to the reactor, with a second control valve which can bypass excess pumped material back to the KOH product storage tank. As soon as KOH flow was established into the reactor vessel 70 through reactor tee 80, the variable speed Acid pump 230 was then immediately started pumping the DPAC solution from tank 20 into reactor tee 80, and likewise through the system into reactor vessel 70, at an acid pumping rate of approximately 16 GPM, or 75% of the anticipated full production capacity to ultimately be achieved, in order to begin the initial reaction. Almost immediately a pulsing jet like roaring like sound was heard from the reactor vessel 70, as the reactants impinged, in a violent reaction in the tee 80. Also immediately a pulsing, tall steam plume began evolving out of the top of reactor vessel 70 in uneven bursts, indicating an unbalanced reaction in the tee 80. Temperature gauge 100 immediately began to rapidly climb from ambient temperature to about 100° C. After evaluating the startup process and observing their were no anomalies the DPAC pumping RPM and pumping rate were increased slowly to approximately 21 GPM where the reaction began to smooth out, and the pulsing reaction stopped, the steam plume changed to a smooth, steady stream as the reaction came into perfect balance as the reactor began to run more quietly and efficiently. As the reaction temperature began to rise to near maximum capacity the temperature peaked at about 172° C. In order to establish the maximum reaction run temperature, because daily atmospheric differences can affect both the reaction and the evaporative cooling temperature in this process, the full and optimum reaction temperature was verified by adding slightly more acid to the reaction, where the temperature began to drop off slightly from the maximum just achieved, verifying the maximum reaction temperature of about 172° C. for the balance of this run. At this point pH and specific gravity, product monitoring began as previously specified and the run temperature was adjusted periodically to maintain maximum operating efficiency. The rpm and subsequent output of the DPAC pump was very slightly altered during the run in order to maintain a stable production pH of about 8.00. The run was continuous for 3 hours producing approximately 9,000 gallons of finished product.

No free water was added continuously during the run to the reactor to control final product specific gravity, which was allowed to climb to its maximum level and remained constant at 1.57. The reaction temperature did not fluctuate and remained about a constant 172° C. Periodic 1,000 ml subsamples were taken, and combined in a common container and a single representative sample drawn of the entire days run and submitted to a commercial laboratory familiar with testing ammoniated phosphorus compounds for polymerization. Total $P_2O_5$ and Ortho $P_2O_5$ determinations were made in order to determine the "non ortho" or polymerized species using approved industry standard methods which utilize the phospho-molybdate colorimetic analytical procedure, with the highest polymerization results listed below as sample #1, in table 1-1.

Example 2

Example 2 was procedurally similar to example 1, including a run temperature of about 170° C. in tee 80, except that the specific gravity was lowered and closely monitored and maintained at 1.48 by continuously adding free water to the reactor vessel 70 via injection port valve 255 on the suction side of cooling, recirculation and product deliver pump 140. Sampling procedure and handling were also similar to example 1, and the results are listed below as sample #2, in table 1-1, which showed less polymerization because of the added free water and lower specific gravity in the reaction process than the results from example 1.

Example 3

Example 3 was procedurally similar to example 2. The run temperature was about 174° C. in tee 80. The specific gravity was lowered still more and closely monitored and maintained at 1.47 by continuously adding free water to the reactor vessel 70 via injection port valve 255 on the suction side of cooling, recirculation and product deliver pump 140. Sampling procedure and handling were also similar to example 2, and the results are listed below as sample #3, in table 1-1, which showed even less polymerization because of the added free water and lower specific gravity in the reaction process than the results from example 2

Example 4

Example 4 was procedurally similar to example 3. The run temperature was about 170° C. in tee 80. The specific gravity was lowered still more and closely monitored and maintained at 1.45 by continuously adding additional free water to the reactor vessel 70 via injection port valve 255 on the suction side of cooling, recirculation and product deliver pump 140. Sampling procedure and handling were also similar to example 3, and the results are listed below as sample #4, in table 1-1, which showed less polymerization because of the additional, added free water and lower specific gravity in the reaction process than the results from example 3.

TABLE 1-1

| # | pH | SG | Total $P_2O_5$ | Ortho $P_2O_5$ | Total Poly Phosphate | Non Ortho From $H_3PO_3$ | Net Poly Phosphate | Total Percent Polyphosphate | Free $H_2O$ |
|---|------|------|-------|-------|-------|------|-------|-------|------|
| 1 | 8.30 | 1.57 | 23.9% | 6.7%  | 17.2% | 5.4% | 11.8% | 49.3% | None |
| 2 | 8.20 | 1.48 | 23.4% | 15.0% | 8.4%  | 5.3% | 3.1%  | 13.3% | 1X   |
| 3 | 8.00 | 1.47 | 22.8% | 14.4% | 8.4%  | 5.2% | 3.2%  | 14.2% | 2X   |
| 4 | 8.00 | 1.45 | 23.2% | 15.8% | 7.4%  | 5.3% | 2.1%  | 9.3%  | 3X   |

Fertilizers formulated with the Dual Phosphorus Acid Combination (DPAC) solution have a three fold advantage, nutritional, fungicidal and bactericidal with the DPAC solution of this invention, because Phosphate and Phosphite identification, signaling and movement is identical in plants through Phosphate transporters. Plants cannot utilize Phosphites as a nutritional sole source of Phosphorus based on research from the early 1950s. Thus if only Phosphites have been applied, increasing their levels in the plant, and Phosphorus levels were previously low or deficient, the plant is not able to differentiate the difference and interprets through signaling transporters that Phosphorus levels are adequate to sustain plant growth and health, while interfering with many of the Phosphorus deficiency responses in plants and yeast (*Saccharomyces cerevisiae*). This phenomenon is known as "Phosphate Starvation." Various plant genes that express Phosphorus sufficiency are thereby suppressed when Phosphites alone are applied to Phosphorus deficient plants, causing the plant to respond in a normal, adequate Phosphorus healthy way, when in fact the opposite is true, making it much more susceptible to nutritional and disease disorders and ultimately yield losses and perhaps mortality. The DPAC solution of this invention solves this plant signaling problem by simultaneously providing both Phosphate and Phosphite in a homogeneous polymeric bond that signals both Phosphorus nutritional sufficiency within the plant, and in the case of Citrus Greening Disease, Phosphite bacterial logically for disease control as well.

Example 5

Example 5 was conducted in order to determine and show the effectiveness of applying fertilizer mixtures formulated with the DPAC solution as opposed to nutrient solutions formulated only with phosphite. A two fold comparative test was conducted to determine if phosphate starvation could be prevented, and the effectiveness of DPAC formulated solutions to demonstrate effectiveness in order to prevent, suppress or control Huanglongbing, Citrus Greening Disease, a bacterial disease of citrus which is currently threatening citrus crops world wide with extinction. The disease is transmitted by psyllids which are small piercing sucking insects. Huanglongbing symptoms include small yellow leaves with a mottled or blotchy appearance and yellow veins exhibiting mineral deficiencies such as Manganese and Zinc, twig and branch dieback, sparse, small fruit that is abnormal in appearance and fails to color properly, thus the name greening, with aborted seeds and poor juice quality and finally rapid degeneration into a non-productive state and mortality.

In test treatment #1, four DPAC (phosphate and phosphite combination) and micronutrient treatments were made at six week intervals to citrus trees exhibiting moderate to severe Greening symptoms. In treatment #2, four Phosphite alone treatments, with micronutrients was applied. In treatment #1 the Greening symptoms reversed within six months and visually the tree returned to a normal healthy state and productive state. In treatment #2 the Greening symptoms have gotten worse with tree removal the inevitable solution. Treatment #1 shows an ideal level of 0.18% in the leaf tissue Phosphorus levels, while the Phosphorus level in treatment #2, 0.12 percent, is severely deficient. The results are shown in table 2-1.

TABLE 2-1

| # | N | P | K | Mg | Ca | Na | S | B | Zn | Mn | Fe | Cu |
|---|---|---|---|----|----|----|---|---|----|----|----|----|
|   | Percent | | | | | | | PPM | | | | |
| 1 | 3.05 | 0.18 | 1.58 | 0.34 | 5.20 | 0.02 | 0.37 | 80 | 45 | 50 | 90 | 16 |
| 2 | 2.83 | 0.12 | 1.23 | 0.31 | 3.95 | 0.06 | 0.37 | 60 | 29 | 26 | 45 | 7  |

Example 6

Example 6 was conducted in order to show the systemic properties and the bacterial disease control effectiveness of the Potassium Polyphosphite solution produced as a result of this invention as compared to the previously determined Orthophosphite crop non-responses.

Phosphites in general are known to move systemically upward and downward throughout the entire plants vascular system, translocating to the new growth, via both the xylem and the phloem. Orthophosphites, are only registered or recommended for foliar application as "nutritionals", or as a fungicide for certain fungal control. The nutritional efficacy of phosphites, as a source of phosphate, has never been demonstrated and their use as a "nutritional" is simply to skirt pesticide regulatory laws. In cases where soil application was attempted, there was no beneficial crop response and even severe crop has damage occurred. Spray tank mixes with Copper are also avoided because of the occurrence of severe crop damage.

*Xanthomonas citri* subsp. *Citri.*, bacterial citrus canker, is a leaf, fruit, and stem blemishing disease, by the bacterial penetration of the stomatal pores. When weather and high wind-driven rain is not a factor, canker is primarily dispersed, or the plant tissue invaded, as a result of insect damage, mechanical exposure or injury, wounds made by thorns where present, and blowing sand.

The bacterium reproduces in lesions on leaves, stems and fruit, where with free moisture, the bacteria ooze out and spread to new growth and other trees. Initially small lesions occur on leaf surfaces which saturate the intercellular spaces with water, and then destroy epidermal plant cell structure, by secreting cell wall degrading enzymes, toxins and extracellular polysarrharides (EPS). Plants fight off disease pressure through natural, self defense, disease suppression or elimination methods, which occur through rapid cytological action, and by triggering other plant cellular phytoalexin accumulations and metabolic changes and other disease resistance inducers. As a result, tree health is ultimately determined by its cells ability to effectively produce and transport antibacterial disease fighting compounds.

Historically there has been no evidence that Orthophosphites have any control over Citrus canker and their use is not recommended for that purpose and are only recommended and all phosphite based pesticides are registered for fungal diseases only, and not for any bacterial diseases, for foliar application only. As noted above, all Orthophosphites are prohibited from being tank mixed with Copper because of phytotoxicity to plant tissue.

The test was set up for both foliar and soil application, and tank mixes with Copper. Applications of Polyphosphite, both with and without added Copper tank mixed, were made to Citrus trees with severe Citrus canker symptoms. The purpose was to test for any Citrus canker control, phytotoxicity to the trees, and for systemic plant self defense responses. It rapidly became evident that the Polyphosphite was able to demonstrate that pplant self defense mechanisms were activated. Within a week after foliar application and about two weeks after soil application, a yellowing, "walling off halo effect" effect of each individual new lesion, somewhat like a fire line around a forest fire, was observed. This is characteristic of a systemic plant self defense response where walling off of the surface lesions occurs, stopping the lesions from enlarging and spreading to adjoining leaves. There was no plant phytotoxicity of leaf tissue observed from either singular applications of the Polyphosphite or from the tank mix combination with Copper. The disease cycle appeared to be stopped, and further colonization, sporulation, reproduction, and dissemination of the bacteria to the entire tree, and adjoining trees seemed to be achieved. The Polyphosphite was curative, by acting within the fungal cell walls to visually stop, inhibiting further fungal or bacterial growth, by direct toxicity to plant pathogens. This was the observation because inside the yellow halo effect, where the lesion had been, a dry dead spot appeared in about 30 days and ultimately dried out as a black dead spot of tissue, and dropped out of the leaf, leaving an open "shot hole" in the leaf where the lesion had occurred. The second observation made was that apparently natural, self defense mechanisms, systemic acquired resistance (SAR) and induced resistance (IR) were induced because the disease did not spread further in the plant tissue, from the initial lesions.

The tank mix with Copper, as a surface protectant and the Polyphosphite as an internal systemic agent, proved to be a good combination, providing control on the surface of the leaf before infection and systemic post control of bacterial sporulation incubation.

The invention as fully described above may embody other specific forms or variations without departing from its spirit or essential characteristics. In that regard, the embodiments described above are to be considered in all respects as illustrative and not restrictive, the scope of the invention being indicated by the claims rather than by the foregoing description and any and all changes that come within the meaning and range of equivalency of the claims are intended to be embraced therein.

We claim:

1. A process for the manufacture of an aqueous fungicide, bactericide and fertilizer solution comprising the following steps:
    (1) dissolving phosphorous acid in phosphoric acid to form a solution of an acid mixture;
    (2) reacting the acid mixture of step (1) with an aqueous potassium hydroxide solution at a temperature of about 65° C. to about 260° C. in a continuous reactor while maintaining the ratio of potassium to phosphorus in a molar ratio of about 1:1 to about 2:1 thereby forming a reaction mixture comprising potassium phosphates, potassium polyphosphates, potassium phosphites, and potassium polyphosphites and potassium phosphate phosphite copolymers; and
    (3) cooling the reaction mixture rapidly at least 1° C. to 60° C., to below about 35° C. to about 65° C.

2. The process of claim 1 wherein the acid mixture comprises about 50-90 parts phosphoric acid and 10-50 parts phosphorous acid.

3. The process of claim 1 wherein the continuous reactor is a tubular pipe reactor and the acid mixture is fed into the tubular reactor at a rate of about 15 to 30 gallons per minute simultaneously with the aqueous potassium hydroxide solution which is being fed into the reactor at a rate of about 20-40 gallons per minute and the acid mixture and potassium hydroxide solution are reacted for about 0.01-1.5 minutes.

4. The process of claim 3 wherein the aqueous potassium hydroxide solution comprises about 40-60% by weight potassium hydroxide.

5. The process of claim 4 wherein cooling of the reaction mixture comprises passing the reaction mixture through a steam disengagement unit whereby water present in the reaction mixture is vaporized thereby rapidly cooling the reaction mixture and the reaction mixture is further cooled by spraying the mixture into an air stream and recycling reaction mixture with reaction mixture entering cooling area thereby rapidly cooling the reaction mixture to below about 25° C. to about 75° C.

6. The aqueous solution made according to claim 1 having a pH of about 6.00 to about 8.50.

7. The aqueous solution of claim 6, where an effective amount is used as a method of treating a plant for fungal and bacterial infection.

8. The aqueous solution of claim 6, where an effective amount is used as a method of treating a plant for a microbial infection, fungal infection, bacterial infection or a combination thereof.

9. The aqueous solution of claim 6, where an effective amount is used as a method of fertilizing a plant.

10. The aqueous solution of claim 6 further comprising agricultural components selected from the group consisting of nitrogen compounds, secondary nutrients, micronutrients and any mixtures thereof.

11. A process for the manufacture of an aqueous fungicidal and bactericidal solution having fertilizer properties comprising the following steps:
(1) combining phosphorous acid and phosphoric acid to form an acid mixture;
(2) reacting the acid mixture of step (1) with an aqueous potassium hydroxide solution at a temperature of about 50 to about 200° C. in a continuous reactor while maintaining the ratio of potassium to phosphorus in a molar ratio of about 1:1 to about 2:1 thereby forming an aqueous potassium polyphosphite solution comprising potassium phosphites, dipotassium phosphite, and potassium polyphosphites; and,
(3) cooling the reaction mixture rapidly at least 25° C. to below about 25° C. to about 75° C.

12. The process of claim 11 wherein the continuous reactor is a tubular pipe reactor and the aqueous acid solution is fed into the tubular reactor at a rate of about 15 to 30 gallons per minute simultaneously with the aqueous potassium hydroxide solution which is being fed into the reactor at a rate of about 20-40 gallons per minute and the acid mixture and potassium hydroxide solution are reacted for about 0.01-1.5 minutes.

13. The process of claim 11 wherein the aqueous potassium hydroxide solution comprises about 40-60% by weight potassium hydroxide.

14. The process of claim 4 wherein cooling of the aqueous potassium polyphosphite solution comprises passing the solution through a steam disengagement unit whereby water present in the aqueous potassium polyphosphite solution is vaporized thereby rapidly cooling the aqueous potassium polyphosphite solution and the solution is further cooled by spraying the solution into an air stream and recycling the aqueous potassium polyphosphite solution with the solution entering cooling area thereby rapidly cooling the reaction mixture from below about 25 to about 75° C.

15. The aqueous potassium polyphosphite solution made according to claim 11 having a pH of about 6.00 to about 8.50.

16. The aqueous potassium polyphosphite solution of claim 15, where an effective amount is used as a method of treating a plant having either fungal infection and or bacterial infection.

17. The aqueous potassium polyphosphite solution of claim 15, where an effective amount is used as a method of treating a plant having either, or any combination of, a microbial fungal or bacterial infection.

18. The aqueous potassium polyphosphite solution of claim 15, where an effective amount is used as a method of fertilizing plants.

19. The aqueous potassium polyphosphite solution of claim 15 further comprising agricultural components selected from the group consisting of nitrogen compounds, secondary nutrients, micronutrients and any mixtures thereof.

20. A dual phosphorus acid combination solution formed by dissolving phosphorous acid in phosphoric acid in a ratio of about 1-99 parts to 99-1 parts.

21. The dual phosphorus acid combination solution of claim 20 further comprising a second agricultural compound.

22. A batch process for the manufacture of an aqueous fungicide, bactericide and fertilizer solution comprising the following steps:
(1) dissolving phosphorous acid in phosphoric acid to form a solution of an acid mixture;
(2) reacting the acid mixture of step (1) with an aqueous potassium hydroxide solution while controlling the temperature at about 50° to about 200° C. in a temperature controlled reactor and controlling the ratio of potassium to phosphorus in a molar ratio of about 1:1 to about 2:1 thereby forming a reaction mixture comprising potassium phosphates, potassium polyphosphates, potassium phosphites, and potassium polyphosphites and potassium phosphate phosphite copolymers; and,
(3) cooling the reaction mixture rapidly at least 25° C. to below about 25° C. to about 75° C.

* * * * *